United States Patent
Vignon et al.

(10) Patent No.: US 11,908,110 B2
(45) Date of Patent: Feb. 20, 2024

(54) ULTRASOUND IMAGING SYSTEM WITH IMPROVED DYNAMIC RANGE CONTROL

(71) Applicant: KONINKLIJKE PHILIPS N.V., Eindhoven (NL)

(72) Inventors: Francois Guy Gerard Marie Vignon, Andover, MA (US); David Wesley Clark, Derry, NH (US); Darwin Philip Adams, Lexington, MA (US); David Prater, Andover, MA (US); Aditya Periyapatna Nagendra, Bangalore (IN); Kirthi Radhakrishnan, Cambridge, MA (US); Roy Allan Sivley, Waltham, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 484 days.

(21) Appl. No.: 17/262,921

(22) PCT Filed: Jul. 19, 2019

(86) PCT No.: PCT/EP2019/069467
§ 371 (c)(1),
(2) Date: Jan. 25, 2021

(87) PCT Pub. No.: WO2020/020761
PCT Pub. Date: Jan. 30, 2020

(65) Prior Publication Data
US 2021/0248724 A1    Aug. 12, 2021

Related U.S. Application Data

(60) Provisional application No. 62/702,682, filed on Jul. 24, 2018.

(51) Int. Cl.
*G06T 5/00* (2006.01)
*G01S 7/52* (2006.01)
*G01S 15/89* (2006.01)
*G06T 5/20* (2006.01)
(Continued)

(52) U.S. Cl.
CPC .......... *G06T 5/009* (2013.01); *G01S 7/52071* (2013.01); *G01S 7/52077* (2013.01);
(Continued)

(58) Field of Classification Search
CPC .......... G06T 5/009; G06T 5/002; G06T 5/20; G06T 5/50; G06T 2200/24;
(Continued)

(56) References Cited

U.S. PATENT DOCUMENTS

| 4,771,470 A * | 9/1988 | Geiser ................. G01S 7/52063 348/625 |
| 5,793,883 A | 8/1998 | Kim et al. |

(Continued)

FOREIGN PATENT DOCUMENTS

CN    103971340 A    8/2014

OTHER PUBLICATIONS

Saim, et al., "Contrast Resolution Enhancement Based on Wavelet Shrinkage and Gray Level Mapping Technique", Tencon 200 Proceedings; IEEE Region 10 Annual Conference, Sep. 24, 2000, pp. 165-170.
(Continued)

*Primary Examiner* — Jose L Couso

(57) ABSTRACT

An ultrasound imaging system has an improved dynamic range control which enables a user to reduce image haze with substantially no effect on bright tissue in the image and without increasing speckle variance. A dynamic range processor processes an input image to produce an approximation image which is a spatially low pass filtered version of the input image. The dynamic range of the approximation image is compressed, and image detail, unaffected by the compression, is added back to produce a dynamically compressed image for display.

15 Claims, 4 Drawing Sheets

(51) Int. Cl.
*G06T 5/50* (2006.01)
*A61B 8/08* (2006.01)

(52) U.S. Cl.
CPC ...... *G01S 7/52084* (2013.01); *G01S 15/8906* (2013.01); *G06T 5/002* (2013.01); *G06T 5/20* (2013.01); *G06T 5/50* (2013.01); *A61B 8/5207* (2013.01); *G06T 2200/24* (2013.01); *G06T 2207/10132* (2013.01); *G06T 2207/20092* (2013.01); *G06T 2207/30048* (2013.01)

(58) Field of Classification Search
CPC . G06T 2207/10132; G06T 2207/20092; G06T 2207/30048; G06T 5/40; G06T 2207/20208; G06T 2207/20004; G01S 7/52071; G01S 7/52077; G01S 7/52084; G01S 15/8906; G01S 7/52033; G01S 7/5206; G01S 7/52069; G01S 15/8993; G01S 7/52046; A61B 8/5207; A61B 8/4483; A61B 8/58; H04N 19/98
See application file for complete search history.

(56) References Cited

U.S. PATENT DOCUMENTS

| | | | |
|---|---|---|---|
| 5,799,111 A * | 8/1998 | Guissin | H04N 19/86 358/463 |
| 5,835,618 A | 11/1998 | Fang et al. | |
| 2003/0187353 A1 * | 10/2003 | Ng | A61B 8/467 600/437 |
| 2007/0047788 A1 * | 3/2007 | Slablaugh | G06T 7/12 382/128 |
| 2007/0083114 A1 * | 4/2007 | Yang | A61B 8/00 600/437 |
| 2007/0093716 A1 * | 4/2007 | Radulescu | G01S 7/5206 600/437 |
| 2010/0022878 A1 | 1/2010 | Azuma et al. | |
| 2011/0054317 A1 * | 3/2011 | Lin | G01S 7/52033 600/443 |
| 2014/0112595 A1 | 4/2014 | Huang | |
| 2015/0317791 A1 | 11/2015 | Fujii | |
| 2015/0348247 A1 * | 12/2015 | McLaughlin | G06T 5/009 382/131 |

OTHER PUBLICATIONS

International Search Report and Written Opinion for International Application No. PCT/EP2019/069467, filed Jul. 19, 2019, 16 pages.
Sikdar, et al., "A Single Mediaprocessor-Based Programmable Ultrasound System", IEEE Transactions on Information Technology in Biomedicine, vol. 7, No. 1, Mar. 2003, pp. 64-70.
Socolinsky, D., "Dynamic range constraints in image fusion and visualization", CiteSeer, in Proc. Signal and Image Processing, 6 pages.

* cited by examiner

# ULTRASOUND IMAGING SYSTEM WITH IMPROVED DYNAMIC RANGE CONTROL

RELATED APPLICATIONS

This application is the U.S. National Phase application under 35 U.S.C. § 371 of International Application No. PCT/EP2019/069467, filed on Jul. 19, 2019, which claims the benefit and priority to Provisional Application No. 62/702,682, filed Jul. 24, 2018, which is incorporated by referenced in its entirety.

TECHNICAL FIELD

This invention relates to ultrasound imaging systems and, in particular, to ultrasound imaging systems with dynamic range controls for adjustment of haze elimination and tissue fill without affecting the dynamic range of image speckle.

BACKGROUND

Ultrasound imaging systems commonly have two user controls for adjustment of the appearance of images, image gain control and image dynamic range control. When a user is observing ultrasound images of a region of interest, these controls are typically adjusted to approve the appearance of the images. For example, a user may be viewing cardiac images of a chamber of a heart containing a blood pool. If the gain is set too high, the blood pool will often be clouded with haze over the heart chamber. The user can reduce or eliminate the haze by turning down the gain, causing the heart chamber to be produced with a desirable solid black shade. While gain reduction will not generally affect image contrast, turning down the gain will undesirably dim the white shading of tissue, which can reduce the clarity and resolution of tissue in the image.

The dynamic range control can also be adjusted to reduce unwanted haze. By turning down or reducing the dynamic range of the displayed image, low-level haze can be diminished and the bright white levels of tissue are largely unaffected as the image contrast increases. But the contrast to noise ratio is unchanged because speckle variance, the range of different grays of speckle in the image, increases with the increase in contrast.

SUMMARY

Aspects of the present invention provide user control which reduces unwanted image haze while leaving bright white tissue shading unaffected, and which accomplishes both without deleteriously increasing the speckle variance.

In accordance with the principles of the present invention, a user gain control is provided which reduces image haze with substantially no effect on the appearance of bright tissue in the image and with improved contrast without increasing speckle variance. In a preferred implementation this is accomplished by a dynamic range processor which processes input image values to produce an approximation image of low spatial frequencies of tissue structure in the image. The difference between the input image and the approximation image contains image detail which preferably contains the speckle characteristic of the image. Dynamic range compression is then applied to the approximation image but not the image detail, which is then recombined with dynamic range adjusted approximation image to produce an image for display. While the dynamic range compression can be accomplished with values prese- lected or optimized by the imaging system, preferably a user control is provided so that the user can adjust the dynamic range processing to produce an image with an appearance that is to the user's liking.

It is understood that one or more processors, either the same processor or different processors, may be used to execute the processes of, e.g., the beamformer, dynamic range processor, image processor.

Figure 1:
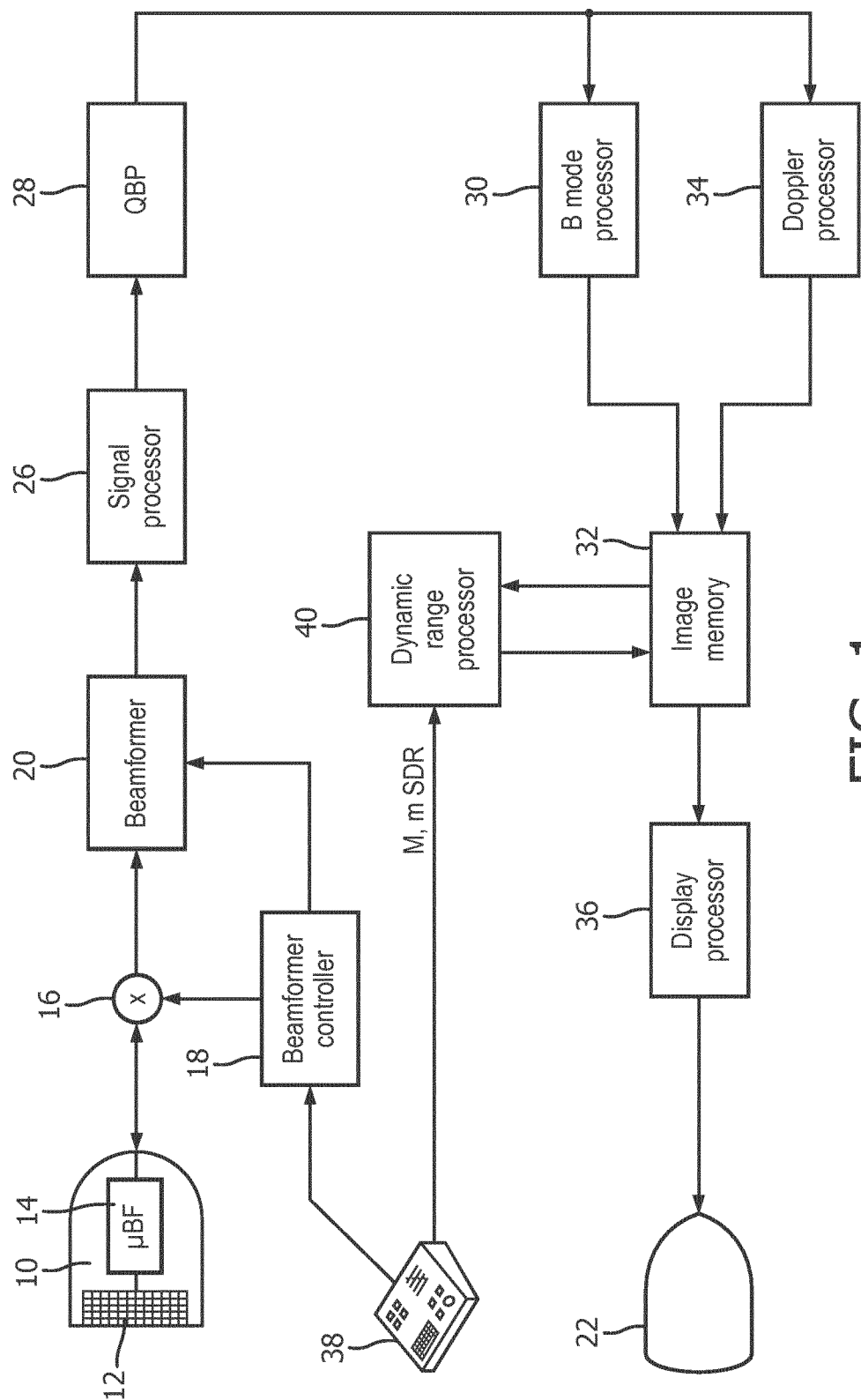
FIG. 1 illustrates in block diagram form an ultrasound system configured in accordance with the principles of the present invention.

Referring first to FIG. 1, an ultrasonic imaging system constructed in accordance with the principles of the present invention is shown in block diagram form. A transducer array 12 is provided in an ultrasound probe 10 for transmitting ultrasonic waves and receiving echo information. The transducer array 12 may be a one- or two-dimensional array of transducer elements capable of scanning in two or three dimensions, for instance, in both elevation (in 3D) and azimuth. The transducer array 12 is coupled to an optional microbeamformer 14 in the probe which controls transmission and reception of signals by the array elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled by the probe cable to a transmit/receive (T/R) switch 16 which switches between transmission and reception and protects the main beamformer 20 from high energy transmit signals. The transmission of ultrasonic beams from the transducer array 12 under control of the microbeamformer 14 is directed by a beamformer controller 18 coupled to the T/R switch and the main beamformer 20, which receives input from the user's operation of the user interface or control panel 38. Among the transmit characteristics controlled by the transmit controller are the number, spacing, amplitude, phase, frequency, polarity, and diversity of transmit waveforms. Beams formed in the direction of pulse transmission may be steered straight ahead from the transducer array, or at different angles on either side of an unsteered beam for a wider sector field of view. For some applications, unfocused plane waves may be used for transmission. Most 1D array probes of relatively small array length, e.g., a 128-element array, do not use a microbeamformer but are driven from and respond directly to the main beamformer.

The echoes received by a contiguous group of transducer elements are beamformed by appropriately delaying them and then combining them. The partially beamformed signals produced by the microbeamformer 14 from each patch are coupled to the main beamformer where partially beamformed signals from individual patches of transducer elements are combined into a fully beamformed coherent echo signal, or echo signals from elements of a one-dimensional array without a microbeamformer are delayed and combined. For example, the main beamformer 20 may have 128 channels, each of which receives a partially beamformed signal from a patch of 12 transducer elements, or from an individual element. In this way the signals received by over 1500 transducer elements of a two-dimensional array transducer can contribute efficiently to a single beamformed signal, and signals received from an image plane are combined.

The coherent echo signals undergo signal processing by a signal processor 26, which includes filtering by a digital filter and optionally noise reduction as by spatial or frequency compounding. The filtered echo signals are coupled to a quadrature bandpass filter (QBP) 28. The QBP performs three functions: band limiting the RF echo signal data, producing in-phase and quadrature pairs (I and Q) of echo signal data, and decimating the digital sample rate. The QBP comprises two separate filters, one producing in-phase samples and the other producing quadrature samples, with each filter being formed by a plurality of multiplier-accumulators (MACs) implementing an FIR filter. The signal processor can also shift the frequency band to a lower or baseband frequency range, as can the QBP.

The beamformed and processed coherent echo signals are coupled to an image processor, a B mode processor 30, which produces B mode images of structure in the body such as tissue. The B mode processor performs amplitude (envelope) detection of quadrature demodulated I and Q signal components by calculating the echo signal amplitude in the form of $(I^2+Q^2)^{1/2}$. The quadrature echo signal components are also coupled to a Doppler processor 34. The Doppler processor 34 stores ensembles of echo signals from discrete points in an image field which are then used to estimate the Doppler shift at points in the image with a fast Fourier transform (FFT) processor. The rate at which the ensembles are acquired determines the velocity range of motion that the system can accurately measure and depict in an image. The Doppler shift is proportional to motion at points in the image field, e.g., blood flow and tissue motion. For a color Doppler image, the estimated Doppler flow values at each point in a blood vessel are wall filtered and converted to color values using a look-up table. The wall filter has an adjustable cutoff frequency above or below which motion will be rejected such as the low frequency motion of the wall of a blood vessel when imaging flowing blood. Either the B mode image or the Doppler image may be displayed alone, or the two shown together in anatomical registration in which the color Doppler overlay shows the blood flow in tissue and vessels in the tissue structure of a B mode image.

The image data produced by the B mode processor 30 and the Doppler processor 34 are coupled to an image data memory 33, where it is stored in memory locations addressable in accordance with the spatial locations from which the image values were acquired. In accordance with the principles of the present invention, sequential B mode images are coupled to a dynamic range processor 40, which processed each image for dynamic range control as described below. The dynamic range adjusted images are coupled back to the image memory, from which they are coupled to a display processor 36 for further enhancement, buffering and temporary storage for display on an image display 22.

Figure 2:
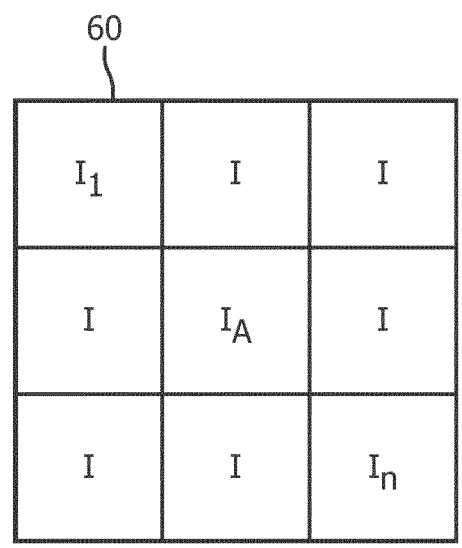
FIG. 2 illustrates a nine-element kernel which may be used to produce an approximation image in accordance with the present invention.

In the illustrated implementation of FIG. 1, the dynamic range processor 40 is an image processor which provides two functions: it computes an approximation image which is preferably a spatial low pass filtered version or speckle-reduced version of a received input image from the image memory, and it performs dynamic range compression of the approximation image to which the image detail absent in the approximation image is thereafter recombined. A simple spatial low pass filter suitable for use in an implementation of the present invention is illustrated conceptually in FIG. 2. This illustration represents a nine-element kernel for spatially processing nine contiguous image elements of an input image I. An image value for an approximation image A is calculated at the central location IA of the kernel by weighting and summing the eight surrounding image values and the central image value of the input image I. Mathematically, this process can be expressed as $$I_A = \sum_{n=1}^{9} \frac{1}{9} I_n \qquad [1]$$

That is, each of the nine image elements of the kernel are weighted by ⅑ and the weighted values of the kernel are then summed to calculate an approximation image value. An approximation image thus will contain primarily low spatial frequency structural information of an image. While this simple example only operates on a small local image area of nine image elements, a preferred kernel size will usually be significantly larger, preferably large enough to encompass input image elements containing a wide (and preferably the full) range of speckle values. Thus, the speckle range can be contained in image "detail" values D, which can be computed as the difference between the input image I and the approximation image A at each image element location, or $$D=I-A \qquad [2]$$

In conventional dynamic range compression, image values below a low brightness level m are mapped to full black, and image values above a high brightness level M are mapped to full white, or $$(I-m)/(M-m) \qquad [3]$$

In an implementation of the present invention, dynamic range compression is applied to the approximation image A but not to the image detail D. An algorithm which performs dynamic range compression in this manner is $$J = 255 \times \left( \max\left(0, \min\left(1, \frac{A-m}{M-m} + \frac{D}{SDR}\right)\right) \right) \qquad [4]$$

Where SDR is the speckle dynamic range. This algorithm is in the form of a mapping expression which will map an input image of values of any bit length to an eight-bit range of zero to 255, a standard display word size. The operation of this algorithm is to map all low-level values of the approximation image A below a level m to black, and all high-level values of the approximation image above a level M to white. The speckle detail D of the original image, determined as shown in expression [2] above, is added back to the dynamic range adjusted approximation image as weighted by the speckle dynamic range SDR, thus preserving the original speckle variance. In a constructed implementation SDR will typically be determined by an optimization process which initially sets SDR to the dynamic range of the input image. As SDR is increased, a smoothing of the image is effected as the speckle variance is decreased. But such smoothing of the image will generally come at the expense of reduced image resolution, as the detail D, while ideally containing only speckle, will in practice include some structural image detail as well.

Figure 3:
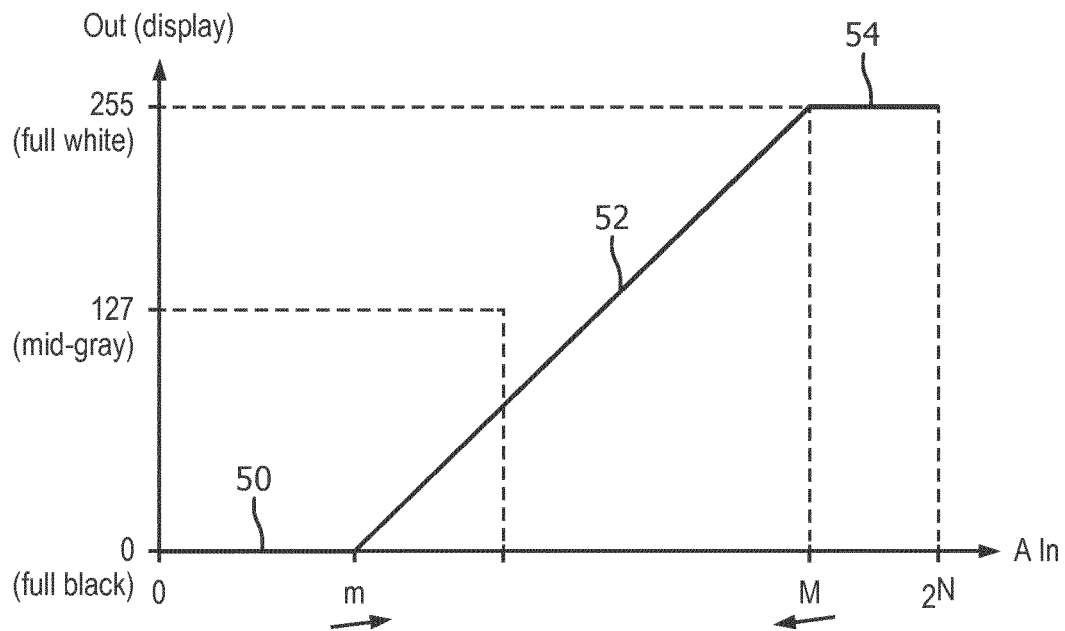
FIG. 3 illustrates a dynamic range curve for an imaging system constructed in accordance with the present invention.

An imaging system can perform the dynamic range processing described above automatically, using preselected values for the variables, preferably accompanied by optimization as greater numbers of images are processed. But preferably the dynamic range processor 40 is controlled by user input from the user interface 38, either in combination with or in substitution for conventional gain and dynamic range controls. An ideal set of controls for many users would be ones that cause chamber darkening (haze reduction) and tissue fill (tissue structure brightening). The dynamic range processor described above can approach this ideal by providing the user with two controls, one which adjusts the value of m for the dynamic range processor and another which adjusts the value of M. As the user adjusts the "m" control to increase the value of m for the processor, low level haze in the image will become increasingly darker. As the user adjusts the "M" control to decrease the value of M, highly echogenic tissue will become increasingly whiter, and with substantially no effect on the haze level, unlike conventional gain adjustment. Alternatively, both variables can be varied by a single control which simultaneously increases m as M is reduced; haze is reduced and tissue is brightened simultaneously. The effects of these individual or combined controls are graphically illustrated in FIG. 3. Without dynamic range compression the compression curve 50-52-54 will be a continuous line from zero at the lower left to 255 (full white in 8-bit nomenclature) at the upper right. As a user control increases m as shown by curve segment 50, all image values from zero to m are set to zero (full black), reducing the appearance of low level haze in the image. As a user control decreases M as shown by curve segment 54, all image values from M to 255 set to full white (255). Dynamic range compression is effected as shown by curve segment 52.

Figure 5:
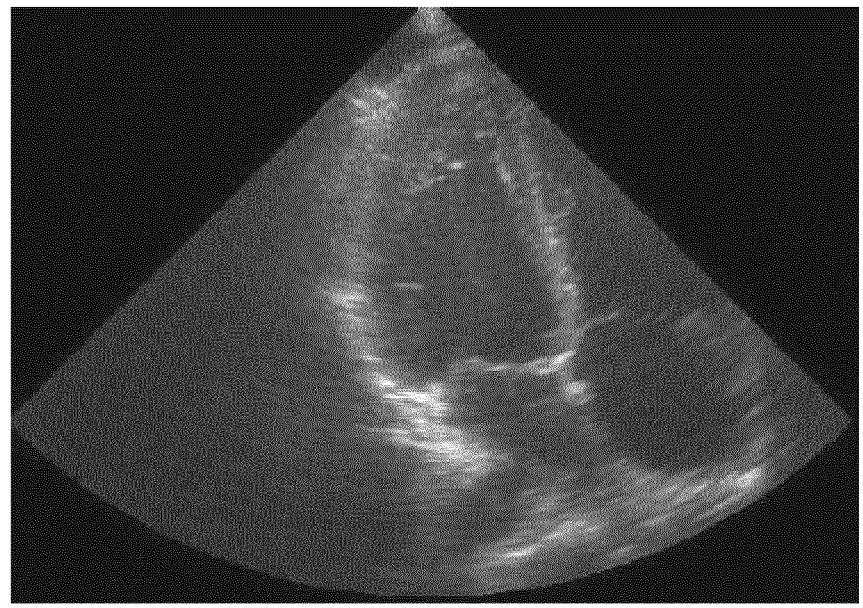
FIG. 5 is a cardiac ultrasound image with unprocessed image speckle and no dynamic range adjustment.
Figure 6:
FIG. 6 is the same cardiac ultrasound image as FIG. 5 after dynamic range adjustment by an ultrasound imaging system of the present invention.

Ultrasound images which illustrate these combined effects are shown in FIGS. 5 and 6. FIG. 5 shows a standard cardiac ultrasound image which is uncompensated for haze and brightening. FIG. 6 shows the same cardiac image with compensation for both. It is seen that the haze in the heart chambers in FIG. 6 has been markedly reduced, and with substantially no degradation of the brightness of the myocardial tissue surrounding the heart chambers.

The combined effects of an implementation of the present invention are summarized in comparison with the effects of standard gain and dynamic range control in the following table:

|  | Haze Reduced | Tissue Brightness Preserved | Speckle Variance Preserved | Contrast | Contrast Noise Ratio |
|---|---|---|---|---|---|
| Gain Reduced | Yes | No | Yes | No Change | No Change |
| Dynamic Range Reduced | Yes | Approx. | No | Increased | No Change |
| Inventive Dynamic Range Reduction | Yes | Approx. | Yes | Increased | Increased |

Figure 4:
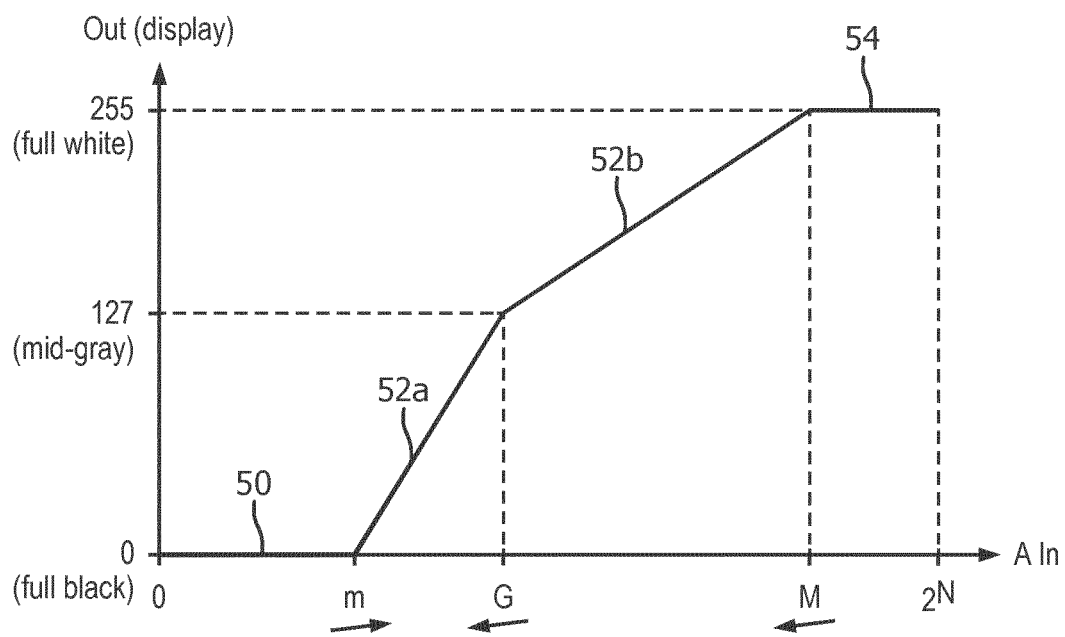
FIG. 4 illustrates a second dynamic range curve for an imaging system constructed in accordance with the present invention which stabilizes mid-range gray values during dynamic range adjustment.

In many ultrasound exams, the mid-gray shades of the B mode image are clinically significant. For instance, myocardial tissue in cardiac images generally appear in mid-gray shades. Thus, it is often important to preserve the character and appearance of mid-gray tones in an image. FIG. 4 illustrates a compression curve which accomplishes this purpose by anchoring mid-gray values about a point G in the compression curve. As m increases to decrease low level haze, mid-gray shades remain fixed about a mid-gray level 127 of the eight-bit scale. Thus, the appearance of myocardial tissue in an image will remain unchanged as m is increased to reduce heart chamber haze. A variation of this control which has been shown to be particularly effective is to tie control of G to M. As M is reduced to increase the brightness of an image, G is also reduced in proportion. This preserves the appearance of myocardial tissue in relation to the appearance of the most echogenic tissue in the image.

Other variations of the inventive dynamic range control described above will readily occur to those skilled in the art. For instance, a user interface control which controls M for brightness can be used to also control the value of SDR, the speckle dynamic range, for the detail D. As the control is adjusted to reduce M and thus increase overall tissue brightness in an image, SDR is concurrently increased, which has the effect of decreasing the speckle variance and smoothing the image as the tissue brightness is increased.

It should be noted that an ultrasound system suitable for use in an implementation of the present invention, and in particular the component structure of the ultrasound system of FIG. 1, may be implemented in hardware, software or a combination thereof. The various embodiments and/or components of an ultrasound system, or components and controllers therein, also may be implemented as part of one or more computers or microprocessors. The computer or processor may include a computing device, an input device, a display unit and an interface, for example, for accessing the internet. The computer or processor may include a microprocessor. The microprocessor may be connected to a communication bus, for example, to access a PACS system or the data network for importing training images. The computer or processor may also include a memory. The memory devices such as the image memory 32 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and display of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules such as a transmit control module, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound imaging system with image dynamic range control comprising:
 a transducer array probe;
 a beamformer coupled to the probe;
 an image processor coupled to the beamformer and configured to produce ultrasound images;
 a dynamic range processor, coupled to the image processor, and adapted produce an approximation image in response to an input image, to apply dynamic range compression to the approximation image, and to add image detail to the dynamic range compressed approximation image; and
 a display, coupled to the dynamic range processor, and adapted to display a dynamic range compressed approximation image with added image detail.

2. The ultrasound imaging system of claim 1, wherein the approximation image further comprises a spatial low pass form of the input image.

3. The ultrasound imaging system of claim 1, wherein the dynamic range processor is further adapted to one or more of converting a low range of image values of the approximation to a black value or converting a high range of image values of the approximation image to a white value.

4. The ultrasound imaging system of claim 1, wherein the image detail further comprises the difference between the input image and the approximation image.

5. The ultrasound imaging system of claim 3, wherein the ultrasound imaging system further comprises a user control coupled to the dynamic range processor.

6. The ultrasound imaging system of claim 5, wherein the user control is further adapted to define the low range of input values to be converted to a black value.

7. The ultrasound imaging system of claim 6, wherein the user control is further adapted to simultaneously define the high range of input values to be converted to a white value.

8. The ultrasound imaging system of claim 5, wherein the user control is further adapted to define the high range of input values to be converted to a white value.

9. The ultrasound imaging system of claim 2, wherein the dynamic range processor is further adapted to produce an approximation image value from a plurality of input image values.

10. The ultrasound imaging system of claim 9, wherein the dynamic range processor is further adapted to spatially low pass filter an input image value with spatially adjacent image input values.

11. The ultrasound imaging system of claim 1, wherein the image detail added to the dynamic range compressed approximation image further comprises speckle dynamic range information.

12. The ultrasound imaging system of claim 11, wherein the image detail added to the dynamic range compressed approximation image further comprises image detail weighted by a speckle dynamic range term.

13. The ultrasound imaging system of claim 12, further comprising a user interface control, coupled to the dynamic range processor, and adapted to enable user variation of the speckle dynamic range term.

14. The ultrasound imaging system of claim 1, further comprising a user control adapted to weight the image detail to be added to the dynamic range compressed approximation image.

15. The ultrasound imaging system of claim 14, wherein the user control is further adapted to smooth the image produced by the display.

* * * * *